United States Patent
Alvarez et al.

(10) Patent No.: US 9,867,635 B2
(45) Date of Patent: *Jan. 16, 2018

(54) METHOD, APPARATUS AND SYSTEM FOR A WATER JET

(71) Applicant: Auris Surgical Robotics, Inc., Redwood City, CA (US)

(72) Inventors: Jeffery B. Alvarez, Redwood City, CA (US); David Mintz, Mountain View, CA (US); Fred Moll, San Francisco, CA (US); Barry Seibel, Pacific Palisades, CA (US)

(73) Assignee: Auris Surgical Robotics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/196,953

(22) Filed: Mar. 4, 2014

(65) Prior Publication Data
US 2015/0025539 A1  Jan. 22, 2015

Related U.S. Application Data

(60) Provisional application No. 61/775,272, filed on Mar. 8, 2013.

(51) Int. Cl.
| | | |
|---|---|---|
| A61B 17/32 | (2006.01) | |
| A61B 17/3203 | (2006.01) | |
| A61F 9/007 | (2006.01) | |
| A61B 34/30 | (2016.01) | |

(52) U.S. Cl.
CPC .......... *A61B 17/3203* (2013.01); *A61F 9/007* (2013.01); *A61F 9/00736* (2013.01); *A61B 34/30* (2016.02)

(58) Field of Classification Search
CPC .. A61F 9/00736; A61F 9/007; A61B 17/3203; A61B 19/2203
USPC .......................................................... 606/107
See application file for complete search history.

(56) References Cited

U.S. PATENT DOCUMENTS

| | | | |
|---|---|---|---|
| 4,597,388 A | 7/1986 | Koziol et al. | |
| 4,905,673 A | 3/1990 | Pimiskern | |
| 5,370,609 A * | 12/1994 | Drasler ............ | A61B 17/32037 604/22 |

(Continued)

FOREIGN PATENT DOCUMENTS

| | | |
|---|---|---|
| JP | H09224951 A | 9/1997 |
| WO | WO 92/14411 A1 | 9/1992 |

(Continued)

OTHER PUBLICATIONS

European search report and search opinion dated Jul. 2, 2015 for EP Application No. 12856685.8.

(Continued)

*Primary Examiner* — Katherine M Shi
(74) *Attorney, Agent, or Firm* — Wilson, Sonsini, Goodrich & Rosati

(57) ABSTRACT

A water jet instrument may be used for manually performing eye surgery such as, cataract, or perform micro-surgery (remove cartilage), or any emulsification technique. The water jet instrument may be manually controlled or controlled by a system with a robotic control. The water jet apparatus defines a jet cutting area that is based at least in part on a flow rate meter and a feedback loop.

19 Claims, 21 Drawing Sheets

(56) References Cited

U.S. PATENT DOCUMENTS

| | | |
|---|---|---|
| 5,425,735 A | 6/1995 | Rosen et al. |
| 5,472,406 A | 12/1995 | De La Torre et al. |
| 5,572,999 A | 11/1996 | Funda et al. |
| 5,662,590 A | 9/1997 | De La Torre et al. |
| 5,695,500 A | 12/1997 | Taylor et al. |
| 6,033,371 A | 3/2000 | Torre et al. |
| 6,326,616 B1 | 12/2001 | Andrien et al. |
| 6,398,792 B1 | 6/2002 | O'Connor |
| 6,406,486 B1 | 6/2002 | De La Torre et al. |
| 6,436,107 B1 | 8/2002 | Wang et al. |
| 6,554,793 B1 | 4/2003 | Pauker et al. |
| 6,638,246 B1 | 10/2003 | Naimark et al. |
| 6,671,581 B2 | 12/2003 | Niemeyer et al. |
| 6,736,784 B1 | 5/2004 | Menne et al. |
| 6,763,259 B1 | 7/2004 | Hauger et al. |
| 7,087,061 B2 | 8/2006 | Chernenko et al. |
| 7,344,528 B1 | 3/2008 | Tu et al. |
| 7,351,193 B2 | 4/2008 | Forman et al. |
| 7,725,214 B2 | 5/2010 | Diolaiti |
| 7,883,475 B2 | 2/2011 | Dupont et al. |
| 7,967,799 B2 | 6/2011 | Boukhny |
| 8,049,873 B2 | 11/2011 | Hauger et al. |
| 8,224,484 B2 | 7/2012 | Swarup et al. |
| 8,414,564 B2 | 4/2013 | Goldshleger et al. |
| 8,518,024 B2 | 8/2013 | Williams et al. |
| 2004/0030349 A1 | 2/2004 | Boukhny |
| 2004/0135733 A1 | 7/2004 | Chou et al. |
| 2005/0070844 A1 | 3/2005 | Chow et al. |
| 2007/0032906 A1 | 2/2007 | Sutherland et al. |
| 2007/0135763 A1 | 6/2007 | Musbach et al. |
| 2007/0299427 A1 | 12/2007 | Yeung et al. |
| 2008/0065109 A1 | 3/2008 | Larkin |
| 2008/0097293 A1 | 4/2008 | Chin et al. |
| 2008/0114341 A1 | 5/2008 | Thyzel |
| 2008/0125698 A1* | 5/2008 | Gerg ............... A61F 9/00736 604/35 |
| 2008/0177285 A1 | 7/2008 | Brock et al. |
| 2008/0187101 A1 | 8/2008 | Gertner |
| 2008/0228104 A1 | 9/2008 | Uber et al. |
| 2009/0171271 A1 | 7/2009 | Webster et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0268015 A1 | 10/2009 | Scott et al. |
| 2009/0312768 A1 | 12/2009 | Hawkins et al. |
| 2009/0326322 A1 | 12/2009 | Diolaiti |
| 2010/0036294 A1 | 2/2010 | Mantell et al. |
| 2010/0073150 A1 | 3/2010 | Olson et al. |
| 2011/0009779 A1 | 1/2011 | Romano et al. |
| 2011/0028887 A1 | 2/2011 | Fischer et al. |
| 2011/0040404 A1 | 2/2011 | Diolaiti et al. |
| 2011/0046441 A1 | 2/2011 | Wiltshire et al. |
| 2011/0106102 A1 | 5/2011 | Balicki et al. |
| 2011/0306836 A1 | 12/2011 | Ohline et al. |
| 2011/0313343 A1* | 12/2011 | Milutinovic ........ A61F 9/00736 604/22 |
| 2012/0138586 A1 | 6/2012 | Webster et al. |
| 2012/0283747 A1 | 11/2012 | Popovic |
| 2013/0144116 A1 | 6/2013 | Cooper et al. |
| 2014/0012276 A1 | 1/2014 | Alvarez |
| 2014/0142591 A1 | 5/2014 | Alvarez et al. |
| 2014/0276594 A1 | 9/2014 | Tanner et al. |
| 2014/0309649 A1 | 10/2014 | Alvarez et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0101442 A1 | 4/2015 | Romo |
| 2015/0119637 A1 | 4/2015 | Alvarez et al. |
| 2015/0119638 A1 | 4/2015 | Yu et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |

FOREIGN PATENT DOCUMENTS

| | | |
|---|---|---|
| WO | WO 03/096871 A2 | 11/2003 |
| WO | WO 2004/105849 A1 | 12/2004 |
| WO | WO 2011/161218 A1 | 12/2011 |
| WO | WO 2013/130895 * | 9/2013 |

OTHER PUBLICATIONS

Office action dated May 21, 2015 for U.S. Appl. No. 13/711,440.
Office action dated Jun. 11, 2015 for U.S. Appl. No. 14/158,548.
U.S. Appl. No. 14/578,082, filed Dec. 19, 2014, Alvarez et al.
U.S. Appl. No. 14/583,021, filed Dec. 24, 2014, Romo et al.
International search report and written opinion dated Jan. 27, 2015 for PCT Application No. US2014/062284.
U.S. Appl. No. 14/201,610, filed Mar. 7, 2014, Romo.
U.S. Appl. No. 14/301,871, filed Jun. 11, 2014, Alvarez et al.
U.S. Appl. No. 14/458,042, filed Aug. 12, 2014, Kintz.
U.S. Appl. No. 14/479,095, filed Sep. 5, 2014, Romo et al.
U.S. Appl. No. 14/523,760, filed Oct. 24, 2014, Alvarez et al.
U.S. Appl. No. 62/037,520, filed Aug. 14, 2014, Yu.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Effect of microsecond pulse length and tip shape on explosive bubble formation of 2.78 iLtm Er,Cr;YSGG and 2.94 iLtm Er:YAG laser. Paper 8221-12, Proceedings of SPIE, vol. 8221 (Monday Jan. 23, 2013).
Ehlers, et al. Integration of a spectral domain optical coherence tomography system into a surgical microscope for intraoperative imaging. Investigative Ophthalmology and Visual Science 52.6. 2011; 3153-3159.
Hubschman. Robotic Eye Surgery: Past, Present, and Future. Journal of Computer Science and Systems Biology. 2012.
International search report and written opinion dated Mar. 29, 2013 for PCT/US2012/069540.
International search report and written opinion dated Nov. 7, 2014 for PCT Application No. US2014/041990.
International search report dated Jun. 16, 2014 for PCT/US2014/022424.
Office action dated Jun. 19, 2014 for U.S. Appl. No. 13/868,769.
Stoyanov. Surgical vision. Annals of Biomedical Engineering 40.2. 2012; 332-345. Published Oct. 20, 2011.
U.S. Appl. No. 14/542,373, filed Nov. 14, 2014, Romo et al.
U.S. Appl. No. 14/542,387, filed Nov. 14, 2014, Bogusky et al.
U.S. Appl. No. 14/542,403, filed Nov. 14, 2014, Yu et al.
U.S. Appl. No. 14/542,429, filed Nov. 14, 2014, Romo et al.
Office action dated Oct. 7, 2014 for U.S. Appl. No. 13/711,440.

\* cited by examiner

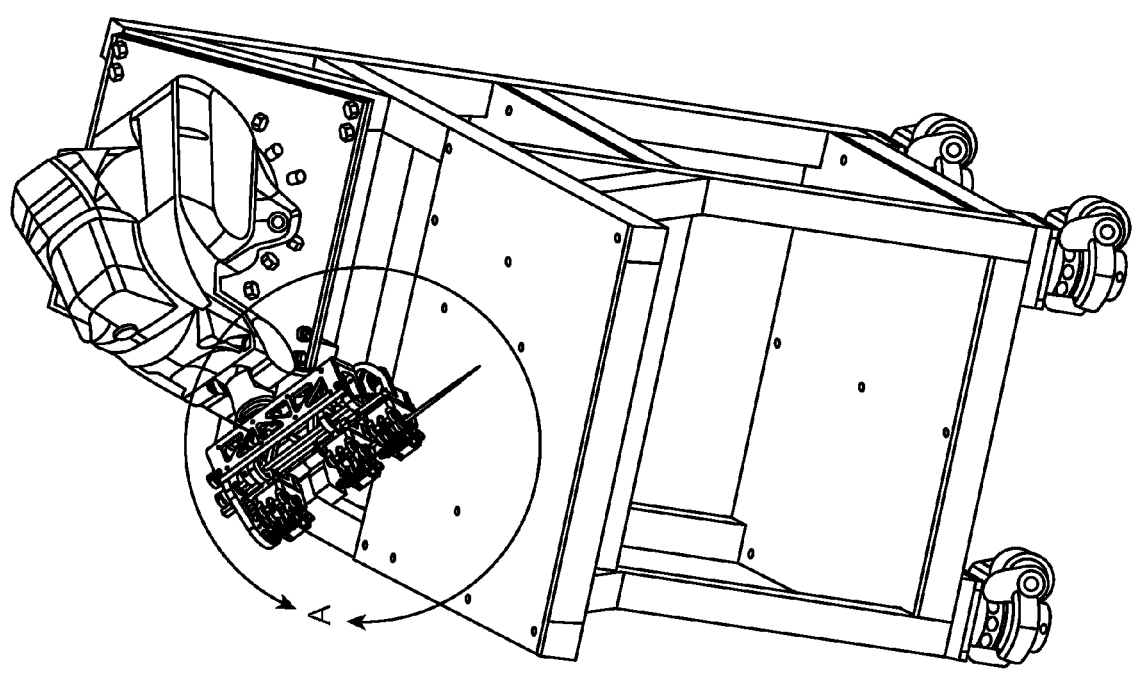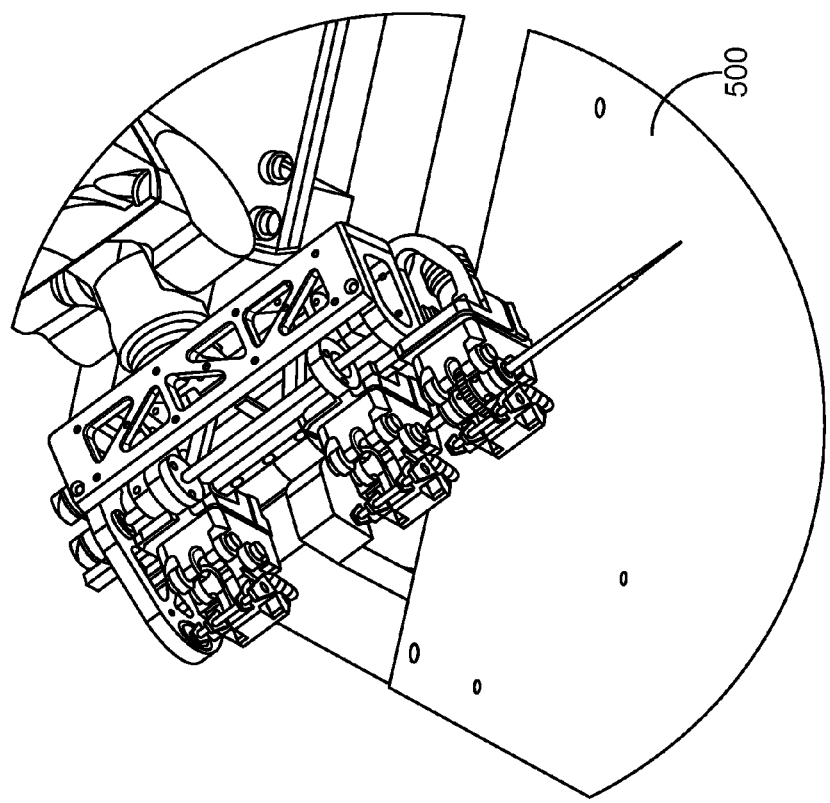
FIG. 5

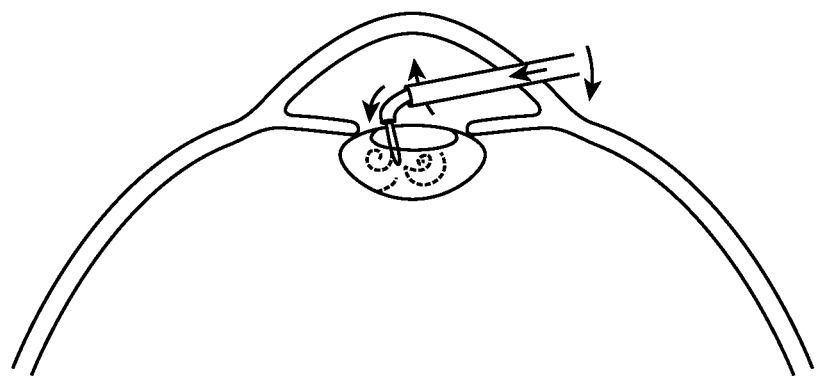
TOP VIEW
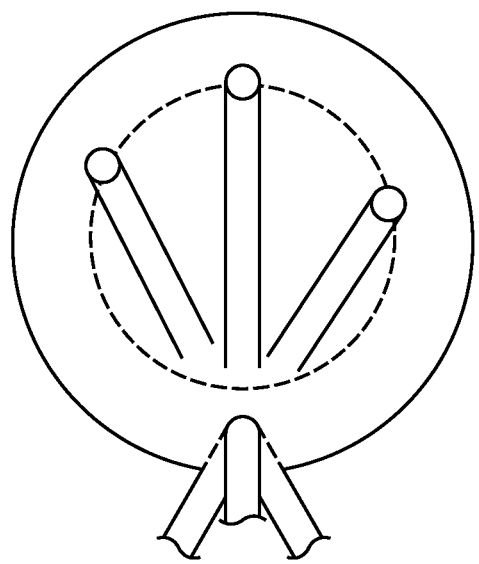
FIG. 7E

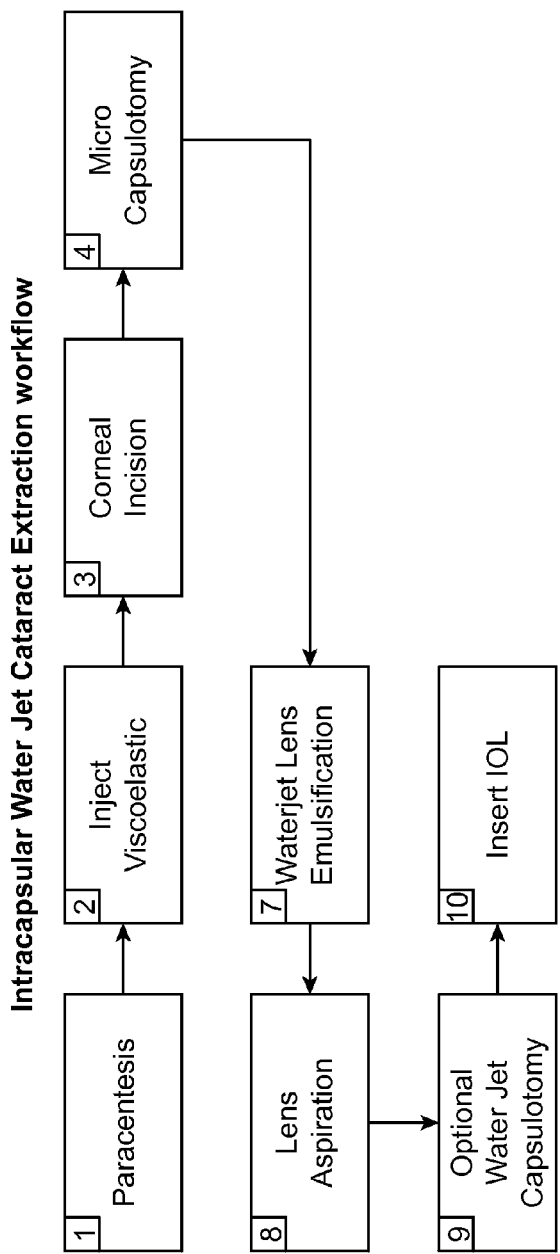
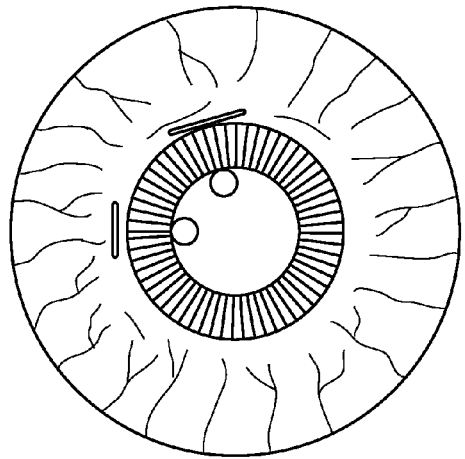
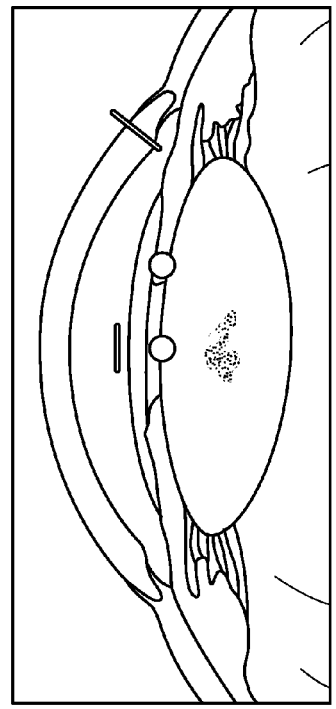
FIG. 9

METHOD, APPARATUS AND SYSTEM FOR A WATER JET

CROSS-REFERENCE TO RELATED APPLICATIONS

This application claims the benefit of U.S. Provisional Application No. 61/775,272, filed Mar. 8, 2013, the entire content of which is incorporated herein by reference.

BACKGROUND OF THE INVENTION

Field of the Invention

The field of the present application pertains to medical devices. More particularly, the field of the invention pertains to an apparatus, system, and method for performing surgery.

Description of the Background Art

A cataract is a clouding of the lens in the eye that affects vision. Most cataracts are related to aging. Cataracts are very common in older people. By age 80, more than half of all Americans either have a cataract or have had cataract surgery.

The lens lies behind the iris and the pupil. It works much like a camera lens. It focuses light onto the retina at the back of the eye, where an image is recorded. The lens also adjusts the eye's focus, letting us see things clearly both up close and far away. The lens is made of mostly water and protein. The protein is arranged in a precise way that keeps the lens clear and lets light pass through it. But as we age, some of the protein may clump together and start to cloud a small area of the lens. This is a cataract. Over time, the cataract may grow larger and cloud more of the lens, making it harder to see.

Age-related cataracts can affect vision in two ways. First, clumps of protein reduce the sharpness of the image reaching the retina. The lens consists mostly of water and protein. When the protein clumps up, it clouds the lens and reduces the light that reaches the retina. The clouding may become severe enough to cause blurred vision. Most age-related cataracts develop from protein clumping. Second, the clear lens slowly changes to a yellowish/brownish color, adding a brownish tint to vision. As the clear lens slowly colors with age, it may gradually cause vision to have a brownish shade. At first, the amount of tinting may be small and may not cause a vision problem. Over time, increased tinting may make it more difficult to read and perform other routine activities.

Surgery is the only real treatment for cataracts. Each year, cataract surgeons in the United States perform over three million cataract surgeries. One of the more conventional cataract surgery procedures is called extracapsular cataract extraction (ECCE). Extracapsular cataract extraction involves the removal of almost the entire natural lens while the elastic lens capsule (posterior capsule) is left intact to allow implantation of an intraocular lens. It involves manual expression of the lens through a large (usually 10-12 mm) incision made in the cornea or sclera. Although it requires a larger incision and the use of stitches, the conventional method may be indicated for patients with very hard cataracts or other situations in which phacoemulsification is problematic.

Modern cataract surgery is usually performed using a microsurgical technique called phacoemulsification, whereby the cataract is emulsified with an ultrasonic handpiece and then suctioned out of the eye. Before phacoemulsification can be performed, one or more incisions are made in the eye to allow the introduction of surgical instruments. The surgeon then removes the anterior face of the capsule that contains the lens inside the eye. A phacoemulsification probe is an ultrasonic handpiece with a titanium or steel needle. The tip of the needle vibrates at ultrasonic frequency to sculpt and emulsify the cataract while a pump aspirates particles through the tip. In some techniques, a second fine steel instrument called a chopper is used from a side port to help with chopping the nucleus into smaller pieces. The cataract is usually broken into two or four pieces and each piece is emulsified and aspirated out with suction. The nucleus emulsification makes it easier to aspirate the particles. After removing all hard central lens nucleus with phacoemulsification, the softer outer lens cortex is removed with suction only. As with other cataract extraction procedures, an intraocular lens implant (IOL), is placed into the remaining lens capsule.

One possible improvement to phacoemulsification is a cataract surgery performed with lasers. Femtosecond Laser cataract surgery is rapidly emerging as a potential technology that may allow for improved precision of incision formation and emulsification of the cataract.

Although phacoemulsification and laser-based cataract surgery work well for many patients, these technologies have several shortcomings. For example, phacoemulsification ultrasound probes must propagate ultrasound energy along the length of the probe, from a proximal transducer to a distal tip. This propagation may lead to transmission of ultrasound energy along the probe to tissues in and around the eye that do not benefit from the transmission. Ultrasound probes also tend to generate more heat than would be desirable for a procedure in the eye. Finally, it may be quite difficult to steer an ultrasound probe around corners or bends, due to the mechanical requirements of propagating the ultrasound wave along the entire instrument. In other words, the probe may have to be rigid or at least more rigid than would be desirable.

Probe based lasers have similar drawbacks. They may generate unwanted heat in the eye and are often difficult to control, thus risking damage to important nearby tissues. They also are easily damaged when attempting to navigate tight corners, as fibers in a laser probe may easily break. Femtosecond laser systems are costly to own and operate and have the additional drawback of extending operative time.

Therefore, it would be advantageous to have a method and device for treating cataracts, and potentially other eye ailments, that included many of the advantages of phacoemulsification and laser procedures without at least some of the drawbacks. Ideally, such a method and device would be relatively simple to manufacture and implement, and would work well for performing cataract surgery without harming surrounding eye tissue. Also ideally, the method and/or device would be applicable to one or more other eye conditions.

Many people worldwide are afflicted by chronic or acute intermittent sinusitis, and it can often be a debilitating disease that affects one's ability to exercise, breathe, fly on airplanes, and the like. Chronic or acute intermittent sinusitis sufferers often experience symptoms such as drainage of a thick, yellow or greenish discharge from the nose or down the back of the throat, nasal obstruction or congestion, causing difficulty breathing through your nose, pain, tenderness and swelling around the eyes, cheeks, nose or forehead, reduced sense of smell and taste, ear pain, aching in the upper jaw and teeth, cough, which may be worse at night, sore throat, bad breath (halitosis), fatigue or irritability and nausea. Several types of surgical procedures have been developed to treat chronic sinusitis, such as functional endoscopic sinus surgery ("FESS") and balloon sinuplasty. FESS is very invasive, however, and requires a long and painful recovery process. Balloon sinuplasty is less invasive but is not effective in all patients.

Some existing solutions are discussed in several issued patents and publications. For example, U.S. Pat. No. 7,967,799 teaches a liquefaction hand-piece tip. However, the tip requires a standoff or spacer to keep the distal end from directly contacting delicate tissue. In another existing solution, United States publication 2004/0030349 creates pulses of fluid. However, the fluid needs to be heated.

Therefore, it would be beneficial to have a new method, apparatus, and system for performing surgery for various applications including eye, micro-surgery, and/or other emulsification applications.

SUMMARY OF THE INVENTION

Embodiments described herein are directed to a method, apparatus, and system for performing surgery for various applications including eye, micro-surgery, and/or other emulsification applications. Specifically, in one embodiment, a water jet apparatus may be used for manually performing eye surgery such as, cataract, or perform micro-surgery (remove cartilage), endoscopic orthopedic surgery, surgery of the ear, or any other procedure requiring removal of tissue in a small confined space. In other embodiments, a system with robotic control of the water jet apparatus may be used. In these embodiments, the water jet apparatus is coupled to a robotic arm via an instrument drive mechanism.

In other embodiments, methods and workflows for cataract extraction are discussed to facilitate the use of the previous apparatus and system embodiments. For example, the workflows depicted are efficient and replace typical steps in a common modern cataract extraction flow. For example, the traditional Hydro dissection, Nuclear fracture, and emsulfication steps are replaced with a single water jet emsulfication step.

In another aspect of the present invention, a method of utilizing the water jet apparatus treating a cataract in an eye may involve controlling a cutting jet area of the water jet based at least in part on a flow rate meter utilizing a feedback loop to a pump.

In another aspect of the present invention, the water jet apparatus utilizes a nozzle that has a jet cutting area and a dispersive area. In one embodiment, the water jet apparatus could be coupled to a system that incorporates a flow rate meter or pressure gauge, pressure vessel or reservoir, and pump. A feedback loop from the flow meter to the pump is controlled by a computer, central processing unit, microcontroller, or any custom application specific integrated circuit (ASIC). In another embodiment, a feedback loop exists at the aspiration pump that is controlled by a computer, central processing unit, microcontroller, or any custom application specific integrated circuit (ASIC). In yet another embodiment, a throttle valve helps to control the flow rate meter based on a feedback loop. All the previous embodiments are discussed in different versions of FIGS. 3A, B, C, and D.

These and other aspects and embodiments will be described in greater detail below, in reference to the attached drawing figures.

BRIEF DESCRIPTION OF THE DRAWINGS

FIG. 5 is an instrument drive mechanism to couple the water jet to a robotic system, according to another embodiment of the present invention.

FIGS. 7A-7G are side, cross-sectional views of a portion of an eye, illustrating a method for using the water jet apparatus to perform cataract surgery, according to one embodiment of the present invention.

FIGS. 9-11 depict a method for a workflow based at least in part on utilizing the previous examples of a water jet apparatus or water jet system in manual or robotic system control, according to one embodiment of the present invention.

DETAILED DESCRIPTION OF THE PREFERRED EMBODIMENT

Figure 1:
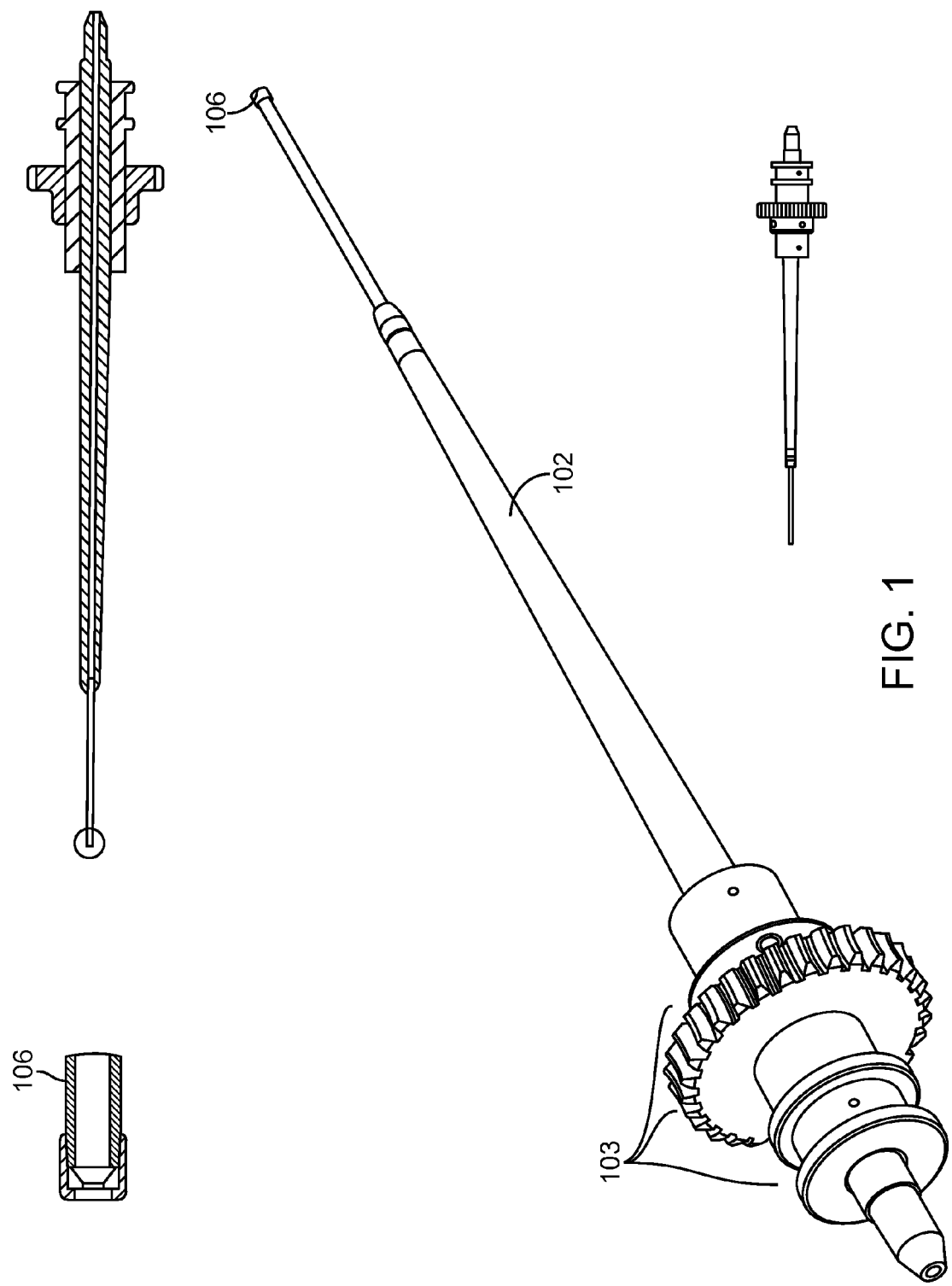
FIG. 1 is a perspective view of a water jet apparatus, according to one embodiment of the present invention.

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The embodiments described herein are directed to method, apparatus, and system for performing surgery for various applications including eye, micro-surgery, and/or other emulsification applications. Specifically, in one embodiment, a water jet apparatus may be used for manually performing eye surgery such as, cataract, or perform micro-surgery (remove cartilage), or any emulsification technique. In the case of a cataract in an eye, a water jet apparatus or system may be used to break apart a cataract into multiple, smaller pieces, which may then be suctioned from the eye using the probe or other suction means. Although the method and device are typically described below in the context of treating cataracts, in various alternative embodiments, other eye conditions may be treated.

In other embodiments, a system with robotic control of the water jet apparatus may be used. In these embodiments, the water jet apparatus is coupled to a robotic arm via an instrument drive mechanism, depicted in connection with FIG. 5. It may be advantageous to incorporate any of the water jet apparatus or water jet system described herein into a robotic surgery/delivery system, such as, the system depicted in FIG. 6. For example, any of the water jet apparatus or water jet systems may be incorporated into the da Vinci® Surgical System, provided by Intuitive Surgical, Inc., or the Magellan™ Robotic System, provided by Hansen Medical, Inc. the RiO, provided by Mako Surgical or Carnegie Mellon's Micron, or John Hopkins University's Steady Hand. Robotic surgical systems such as (but not limited to) these examples may register the water jet apparatus to the target anatomy. Such capability enables both precise and safe movement water jet apparatus such that, when enabled, the fluid is focused in the desired jet cutting area and rapidly dispersed outside of that in order to treat the target tissue and spares injury to surrounding tissue. A number of robotic surgery systems are presently known, and others may be developed specifically for use with the water jet probes and methods described herein.

In other embodiments, methods and workflows for cataract extraction are discussed to facilitate the use of the previous apparatus and system embodiments. For example, the workflows depicted are efficient and replace typical steps in a common modern cataract extraction flow. For example, the common Hydro dissection, Nuclear fracture, and emsulfication steps are replaced with a single water jet emsulfication step. The improved workflows are depicted in connection with FIGS. 9-11.

In another aspect of the present invention, a method of utilizing the water jet apparatus treating a cataract in an eye may involve controlling a cutting jet area of the water jet based at least in part on a flow rate meter utilizing a feedback loop to a pump, as depicted in connection with FIG. 3.

In another aspect of the present invention, the water jet apparatus utilizes a nozzle that generates a jet cutting area and a dispersive area when pressurized water is passed through it into a fluid filled environment, a preferred embodiment uses saline. In one embodiment, the water jet apparatus could be coupled to a system that incorporates a flow rate meter, pressure vessel, and pump. A feedback loop from the flow meter to the pump is controlled by a computer or central processing unit, as depicted in connection with FIG. 3A.

Figure 2:
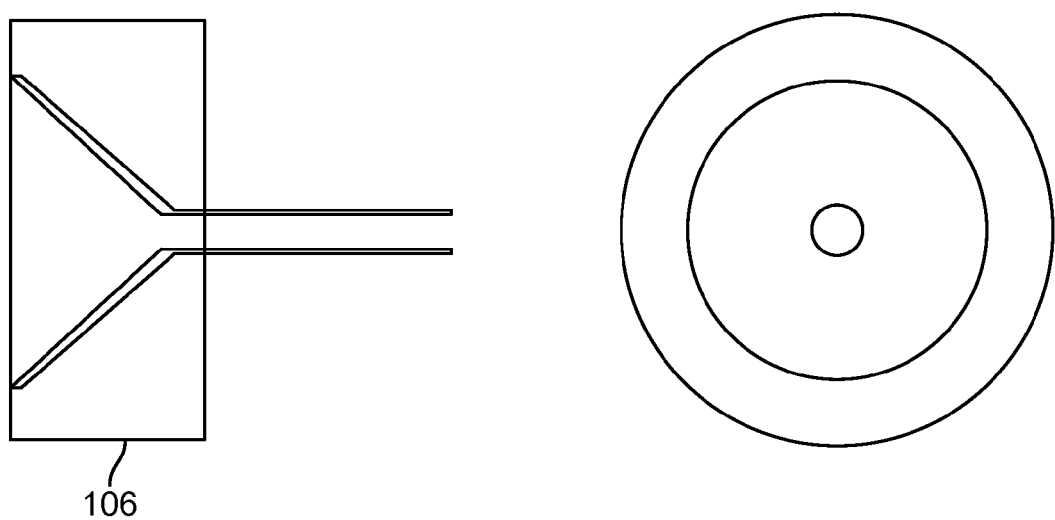
FIG. 2 is a side-view of a portion of a nozzle of the water jet apparatus depicted in FIG. 1.

Referring to FIGS. 1 and 2, one embodiment of a water jet apparatus 102 includes a tip with a nozzle 106 at a distal end and a instrument drive coupling mechanism 103 at a proximal end. The nozzle 106 is depicted in further detail in FIG. 2. In one embodiment, the instrument drive coupling mechanism 103 facilitates coupling to a instrument drive mechanism as depicted in connection with FIG. 5. For this embodiment, the apparatus may be controlled by a robotic system as depicted in connection with FIG. 6 or the previous embodiments depicted in connection with da Vinci® Surgical System, provided by Intuitive Surgical, Inc., or the Magellan™ Robotic System, provided by Hansen Medical, Inc., or Carnegie Mellon's Micron, or John Hopkins University's Steady Hand.

However, in another embodiment, the water jet apparatus 102 would not have an instrument drive coupling mechanism 103 and would be used in a manual and may have a different configuration at the proximal end.

In one embodiment, the water jet apparatus would consist of the probe 102. In another embodiment, the water jet apparatus could be configured to include or support the other block diagrams depicted in connection with FIGS. 3A, B, C, and D.

Referring to FIG. 2, a side-view a portion of a nozzle 106 of the water jet apparatus is depicted. In one embodiment, the nozzle 106 is a sapphire orifice manufactured by Swiss Jewel Company. In this embodiment, the nozzle 106 may have a plurality of different diameter measurements, thickness, angle, and Vee depth as depicted in the table in connection with FIG. 2. However, the claimed subject matter is not limited to neither the different measurements depicted nor configurations implied by the illustration. For instance one skilled in the art appreciates utilizing different measurements or configurations as needed for the particular application or other factors, such as, jet cutting area, dispersive area, pressure levels, exiting location or nozzle orientation.

However, the claimed subject matter is not limited to a sapphire orifice nozzle. One skilled in the art appreciates utilizing not only different nozzle configurations, but also different nozzle material, such as, but not limited to, diamond or stainless steel.

Figure 3A:
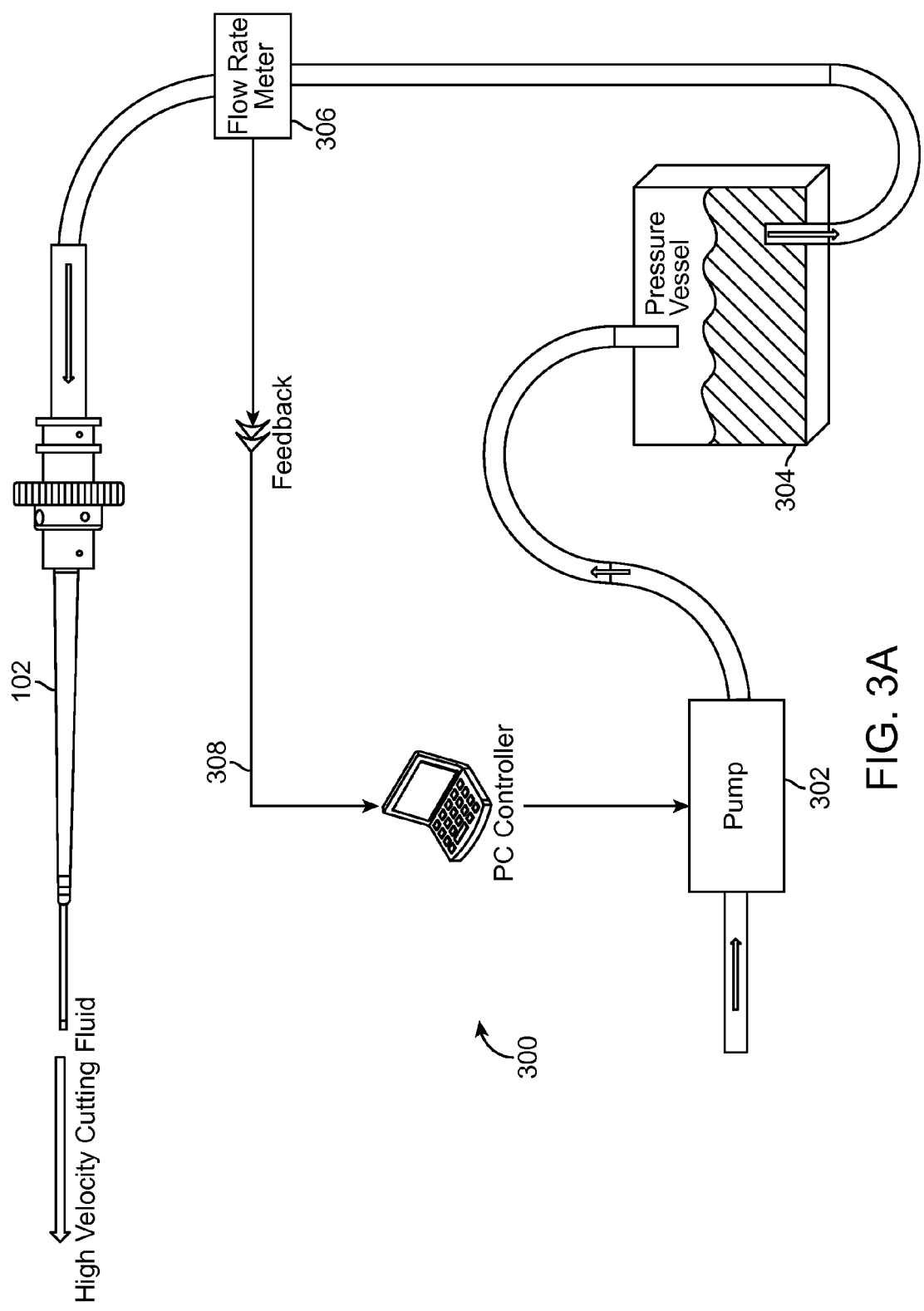
FIGS. 3A, 3B, 3C, 3D, and 3E are a block diagram of a water jet system, according to multiple embodiments of the present invention.

Referring to FIG. 3A, a block diagram of a water jet system 300 is depicted. As discussed earlier, the water jet apparatus 102 of FIG. 1 may incorporate or be coupled to block diagrams depicted in connection with FIGS. 3A, B, C, and D, such as, a pump, pressure vessel, throttle valve, aspiration pump, and flow rate meter.

In one embodiment for a robotic control system, the water jet apparatus 102 is controlled by a robotic system, because the water jet apparatus is coupled to an instrument drive mechanism. For this embodiment, the other blocks depicted, such as, flow rate meter, computer, feedback loop, pump, and pressure vessel, are coupled to the robotic arm while residing near the robotic arm.

In another embodiment, the water jet apparatus 102 includes a pressure vessel, and is controlled by a robotic system, because the water jet apparatus is coupled to an instrument drive mechanism. For this embodiment, the other blocks depicted, such as, flow rate meter, personal computer, feedback loop, and pump are coupled to the robotic arm while residing near the robotic arm.

In yet another embodiment, the water jet apparatus 102 is manually controlled and may be coupled to the other block diagrams via an interface.

In this water jet system 300, the fluid enters a pump 302 and is forwarded to a pressure vessel 304 via a tube. An output of the pressure vessel is forwarded to the flow rate meter 306. In one embodiment, an output of the flow rate meter is controlled by a feedback loop through a computer and a pump. The feedback loop facilitates the output of the flow rate meter based on a desired jet cutting area of an output of the nozzle 106 from the water jet apparatus.

Figure 3B:
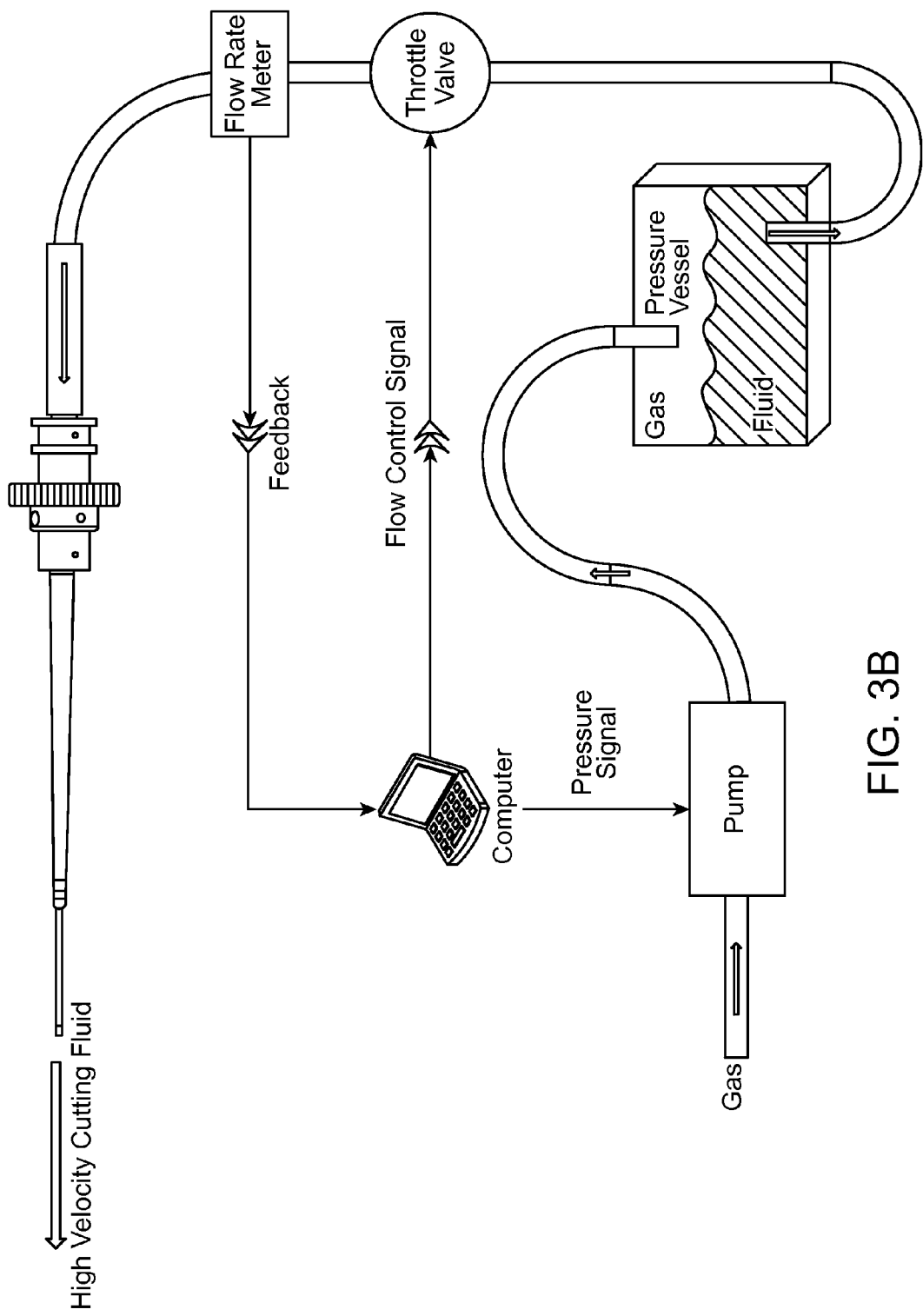
Figure 3C:
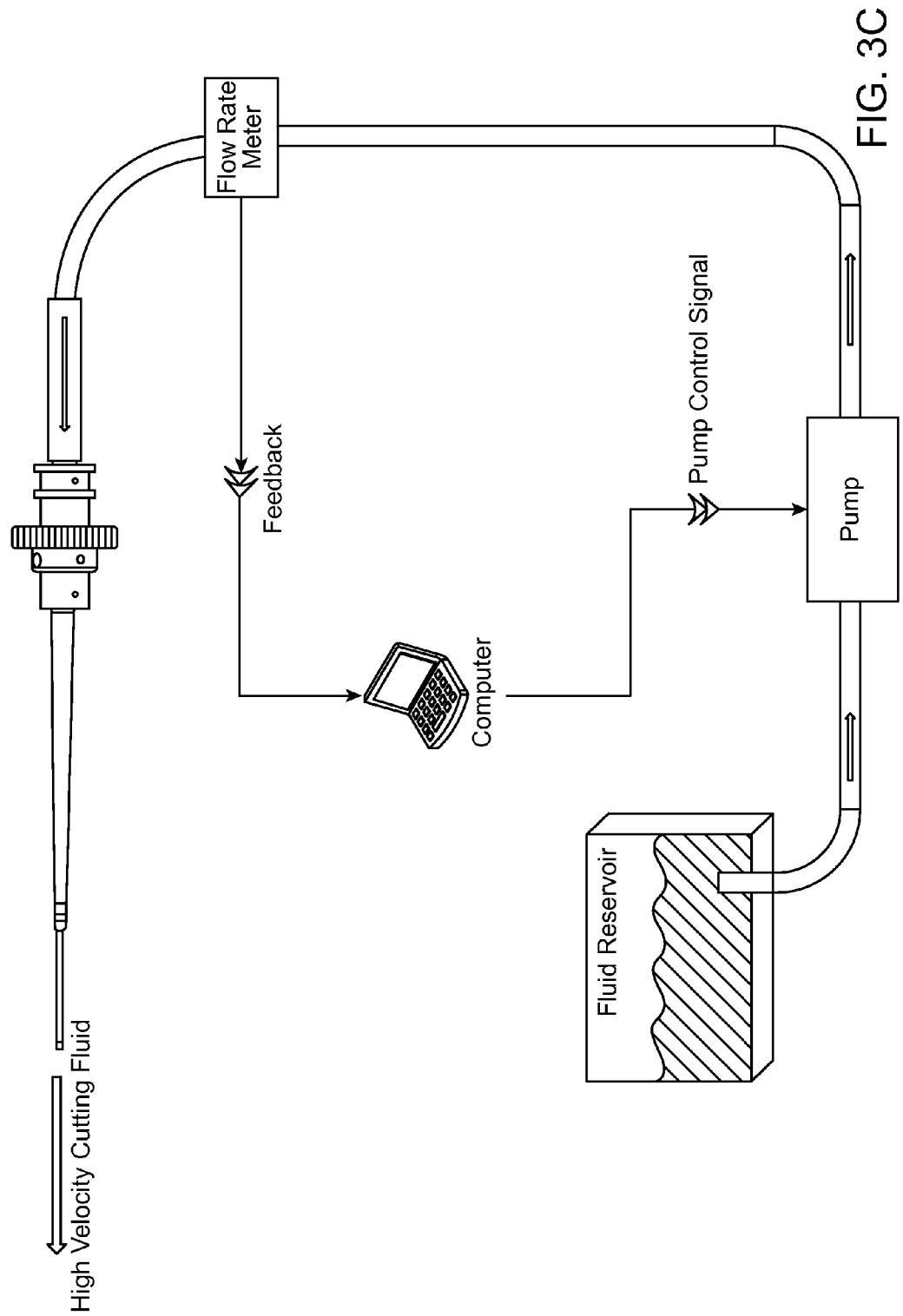

In alternative embodiments, FIG. 3B depicts a throttle valve to help facilitate the flow rate based on a feedback loop. In this embodiment, the throttle valve receives the control signal from either a computer, central processing unit, microcontroller, ASIC, or other control circuitry. In yet another embodiment, FIG. 3C depicts a fluid reservoir coupled to the pump, wherein the feedback loop between the flow rate meter and pump is controlled by a computer, central processing unit, microcontroller, ASIC, or other control circuitry.

Figure 3D:
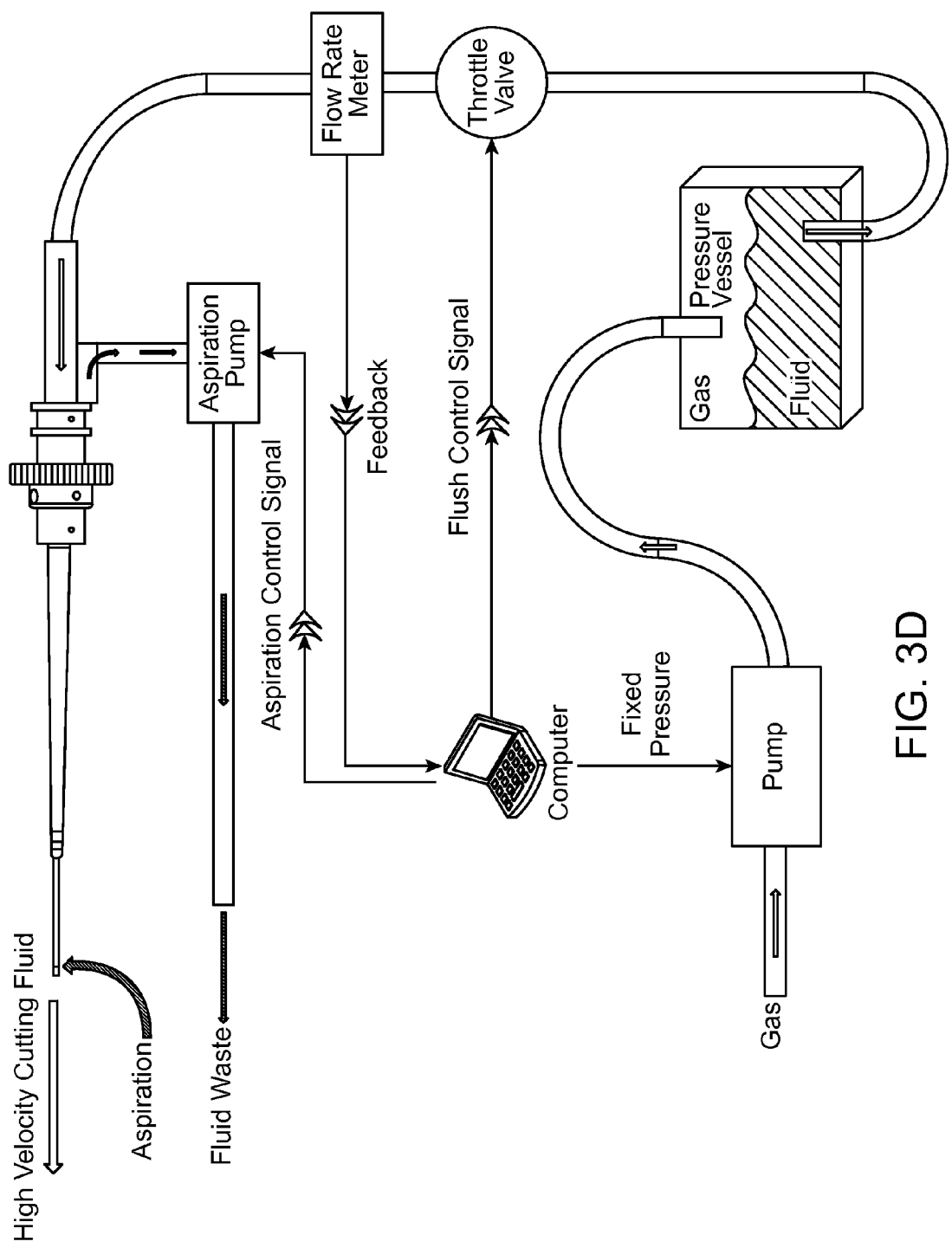

In yet another embodiment, FIG. 3D depicts an aspiration pump that controls removal of material from the operative site. It also has a feedback loop with a flow rate meter that is controlled by a computer, central processing unit, microcontroller, ASIC, or other control circuitry. The aspiration pump may be controlled by the Aspiration flow rate meter feedback signal and or the water jet flow rate meter feedback signal to maintain a desired absolute aspiration flow, or to track the water jet flow in order to maintain the material volume in an enclosed operative space like the interior of the eye. Similarly in this configuration the Water Jet flow may be moderated or interrupted automatically, using the throttle valve or pump control, based on the measured aspiration flow. This may be done in the event that the aspiration path is unable to match the desired flow rate due to blockage, pinched tube, or other mechanical failure.

Figure 3E:
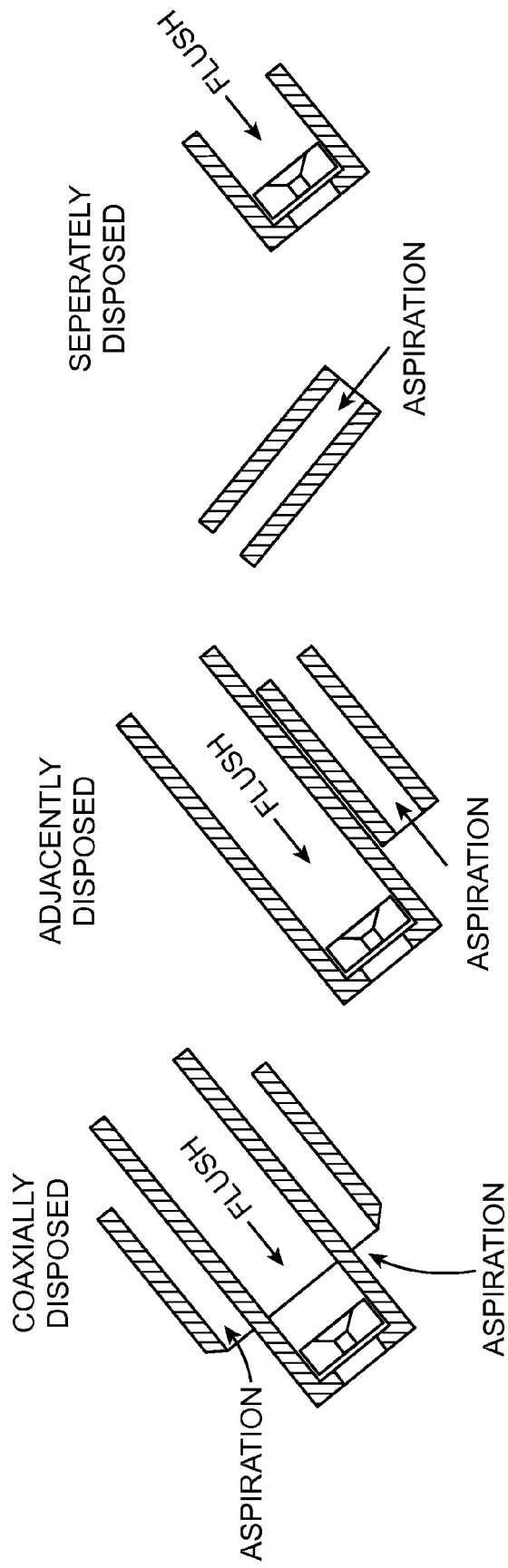

Referring to FIG. 3E, multiple embodiments of water jet system configurations are depicted. The configuration on the left depicts a coaxially disposed configuration of a water jet fluid flush with an aspiration on either side. The configuration in the center depicts an adjacently disposed water jet fluid flush and aspiration in a separate tube. In the embodiment on the far right, the water jet fluid flush and aspiration are separately disposed.

Figure 4:
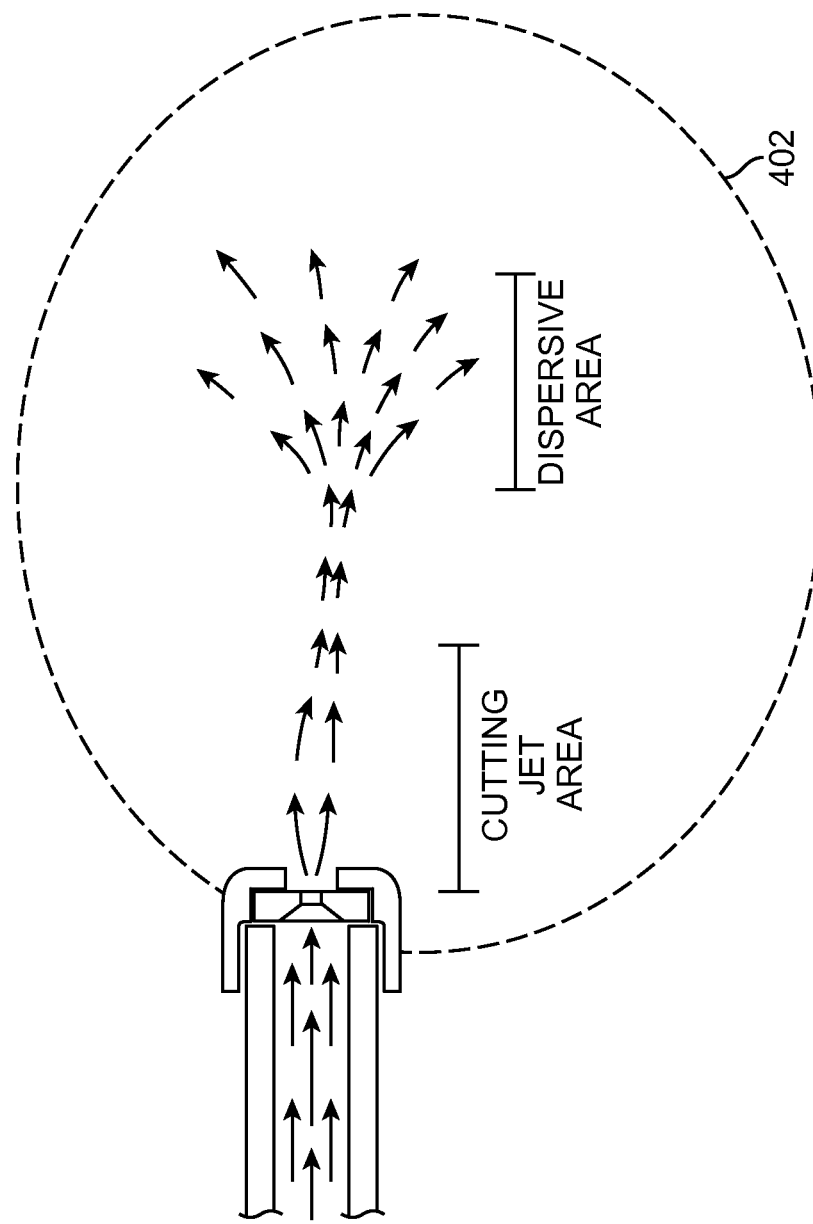
FIG. 4 is a cross section side view of an output of the nozzle with a cutting jet area and dispersive area depicted, according to another embodiment of the present invention.

Referring to FIG. 4, a fluid output of the nozzle 106 is depicted as first a focused cutting jet area and eventually a dispersive area. In one embodiment, the cutting jet area and dispersive area are in a fluid medium 402, such as, a saline solution. As mentioned in connection with FIGS. 3A, B, C, and D, the feedback loops control the flow of fluid to the water jet apparatus 102. For example, if the jet cutting area needs to be increased, the flow rate meter could request an increase in pressure from the pump. Alternatively, if the jet cutting area needs to be decreased, the flow rate meter could request an decrease in pressure from the pump.

Referring to FIG. 5, an instrument drive mechanism to couple the water jet to a robotic system is depicted. In one embodiment, the instrument drive coupling mechanism 103 of FIG. 1 is used to facilitate coupling to the instrument drive mechanism depicted in FIG. 5. For this embodiment, the apparatus may be controlled by a robotic system as depicted in connection with FIG. 6 or the previous embodiments depicted in connection with da Vinci® Surgical System, provided by Intuitive Surgical, Inc., or the Magellan™ Robotic System, provided by Hansen Medical, Inc. or Carnegie Mellon's Micron, or John Hopkins University's Steady Hand.

However, the instrument drive mechanism is not limited to this embodiment. One skilled in the art appreciates modifications to facilitate coupling to different robotic arm configurations.

Figure 6:
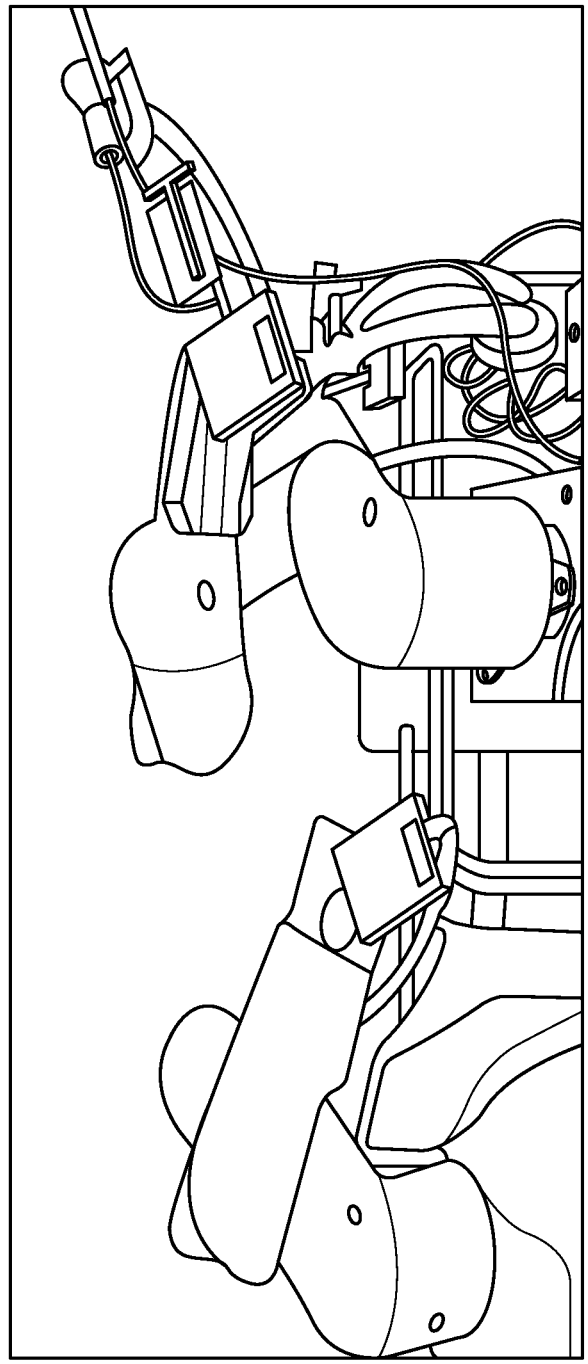
FIG. 6 is a robotic system to control the water jet apparatus or water jet system, according to another embodiment of the present invention.

FIG. 6 is a robotic system to control the water jet apparatus or water jet system. As discussed earlier, the instrument drive mechanism described in FIG. 5 may be used to couple the water jet apparatus or system to facilitate control by this robotic system configuration.

In this embodiment for a robotic control system, two instrument drivers each of which contains an instrument interface that drives a medical instrument is depicted. However, the claimed subject matter is not limited to this particular robotic system and could support any robotic control system with one or more interfaces and one or more instrument drivers. As previously mentioned, various robotic systems facilitate control of the water jet apparatus within the eye. For example, the robotic systems could utilize known localization techniques, such as, 3D imaging, MRI, CT, Ultrasound, Intra operative (OCT), and the like.

Turning now to FIGS. 7A-7G, one embodiment of a method for treating a cataract is illustrated. For convenience, only a distal portion of the probe 102 is illustrated in these figures. Also, in various alternative embodiments of the method, the water jet 102 may either manual or coupled with a robotic surgery system. Thus, the present description may be applied to any delivery method, whether robotic or not. Any suitable imaging system may be incorporated as well, sometimes as part of the robotic system. Three dimensional imaging is but one example.

Figure 7A:
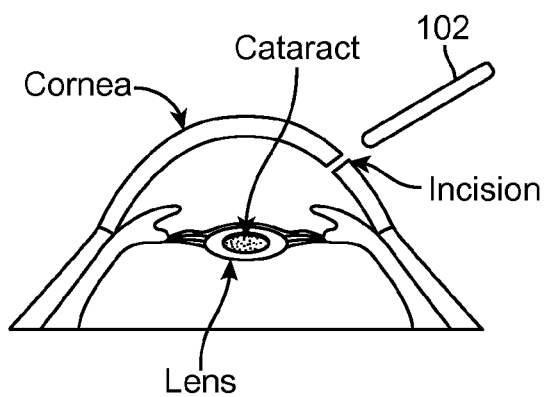
Figure 7B:
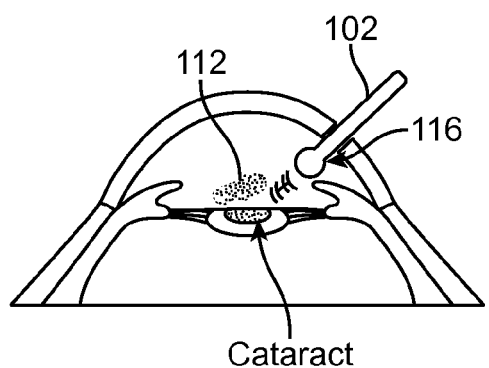
Figure 7C:
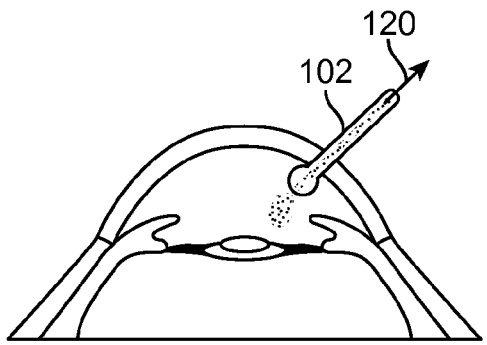

In FIG. 7A, a portion of an eye is shown in cross-section, including a cornea, lens and cataract, with an incision formed in the cornea. The water jet 102 (as described above or some alternative embodiment) may be inserted through the incision, as shown in FIG. 7B. Once the cataract is fully broken up or emulsified, as shown in FIG. 7C, the pieces of cataract may be aspirated. Alternatively, a separate aspiration device may be used. Once the cataract is removed, an intraocular lens (IOL) implant may be implanted, typically through the same incision.

Figure 7D:
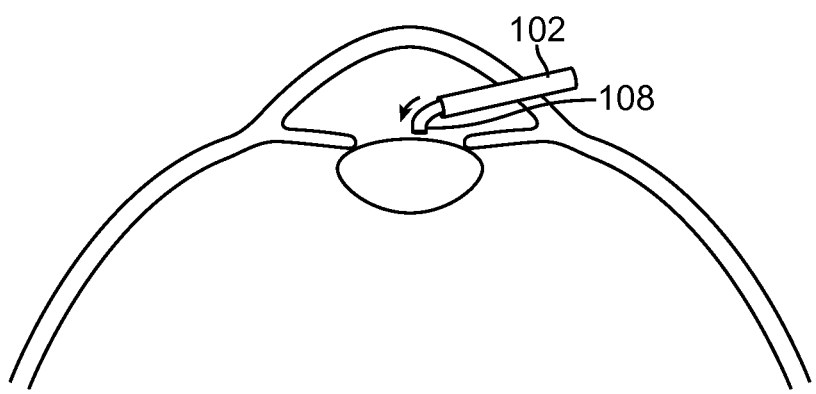
Figure 7F:
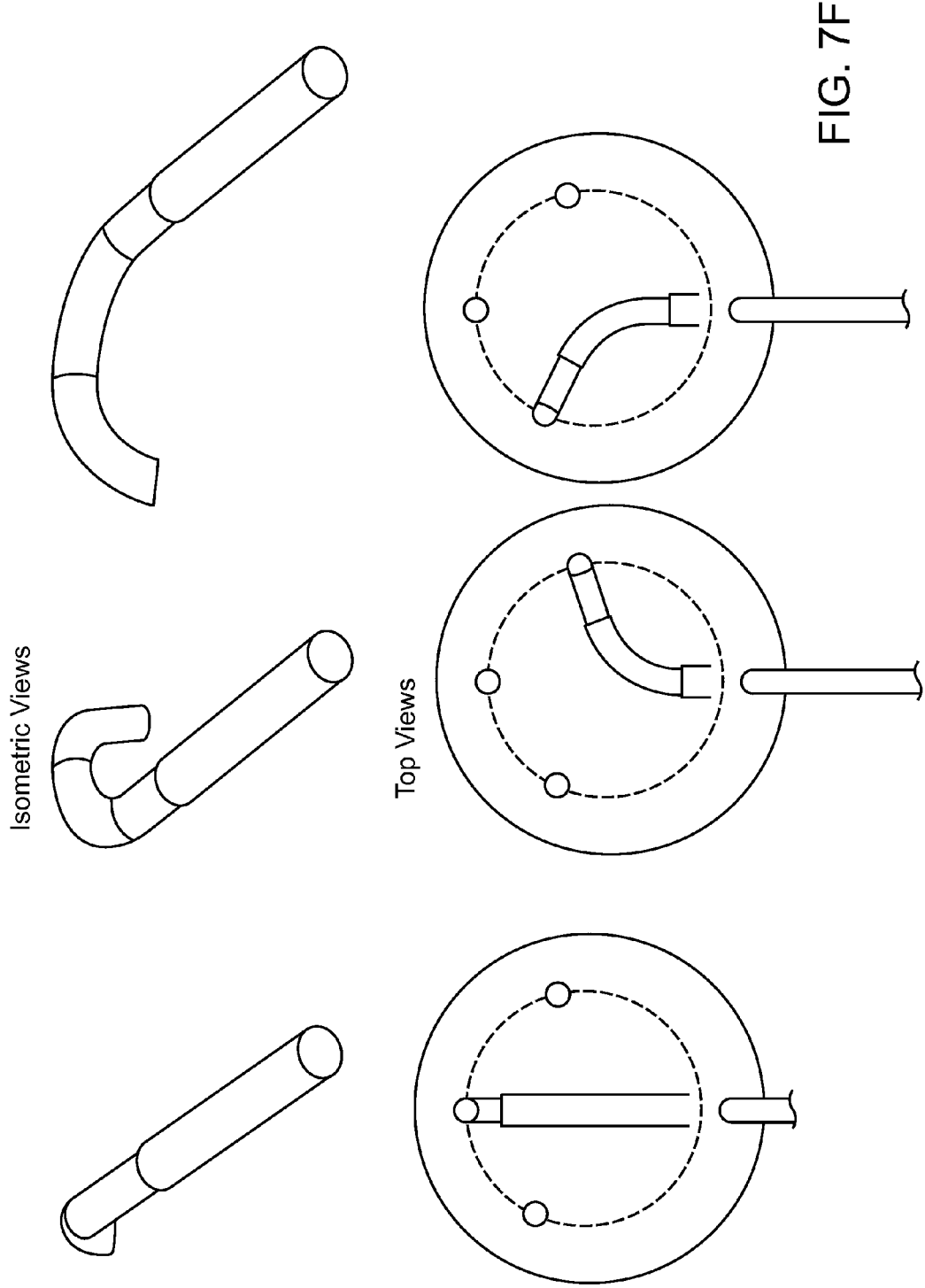
Figure 7G:
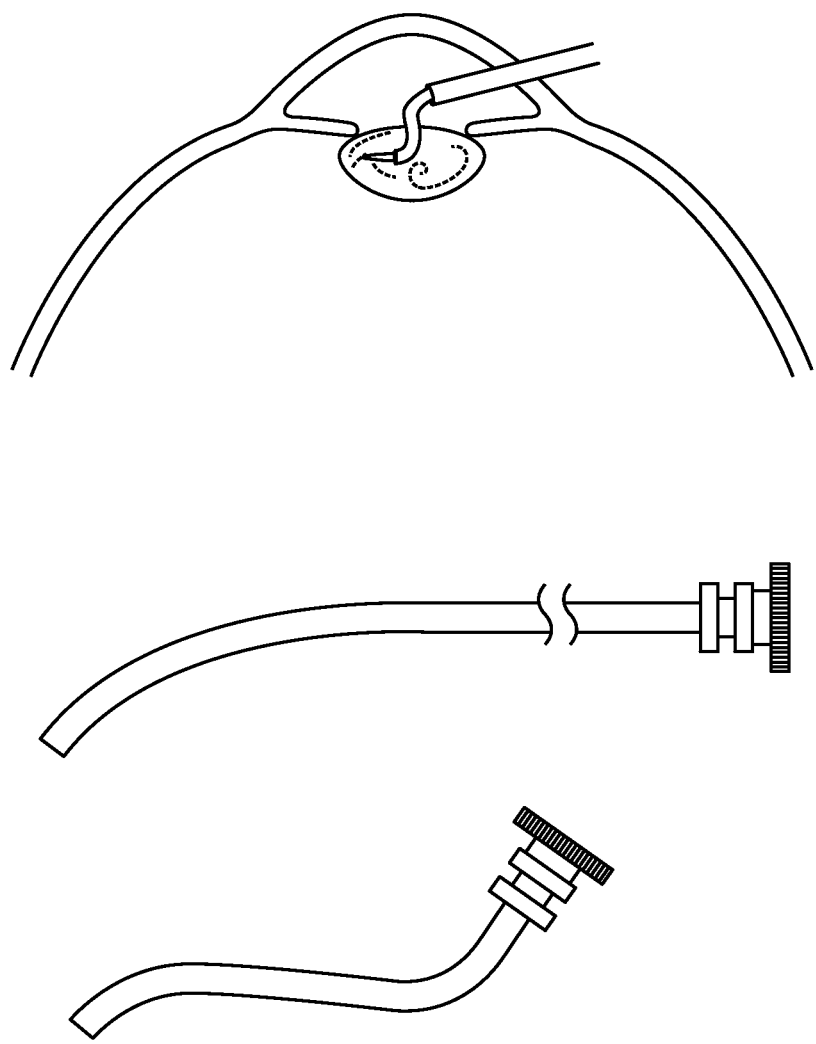

Different instrument configurations for the water jet are depicted in FIG. 7D (bent tube 108 with a nozzle 106), FIG. 7E depicts a pattern of cuts for a circle configuration, as required for a capsulotomy, with a yaw rotation movement of the water jet. The depiction of a circle is for illustrative purposes only, one schooled in the art will realize that other shapes or patterns can be generated manually or under robotic control as required by the surgical procedure. FIG. 7F depicts an isometric view and a top view of a plurality of shaped tubes, axially translatable to vary articulation angle, and configured to reduce proximal motion of the instrument, while enabling complex distal tip motion. FIG. 7G depicts multiple potentially retractable tip configurations for the water jet apparatus.

In alternative embodiments, any other suitable type of articulation mechanism may be used to articulate the water jet apparatus. Examples include, but are not limited to, concentric shaped tubes, flexures, pivot joints, cam mechanisms, pull wire enabled bending, slotted tubes and the like.

Figure 8:
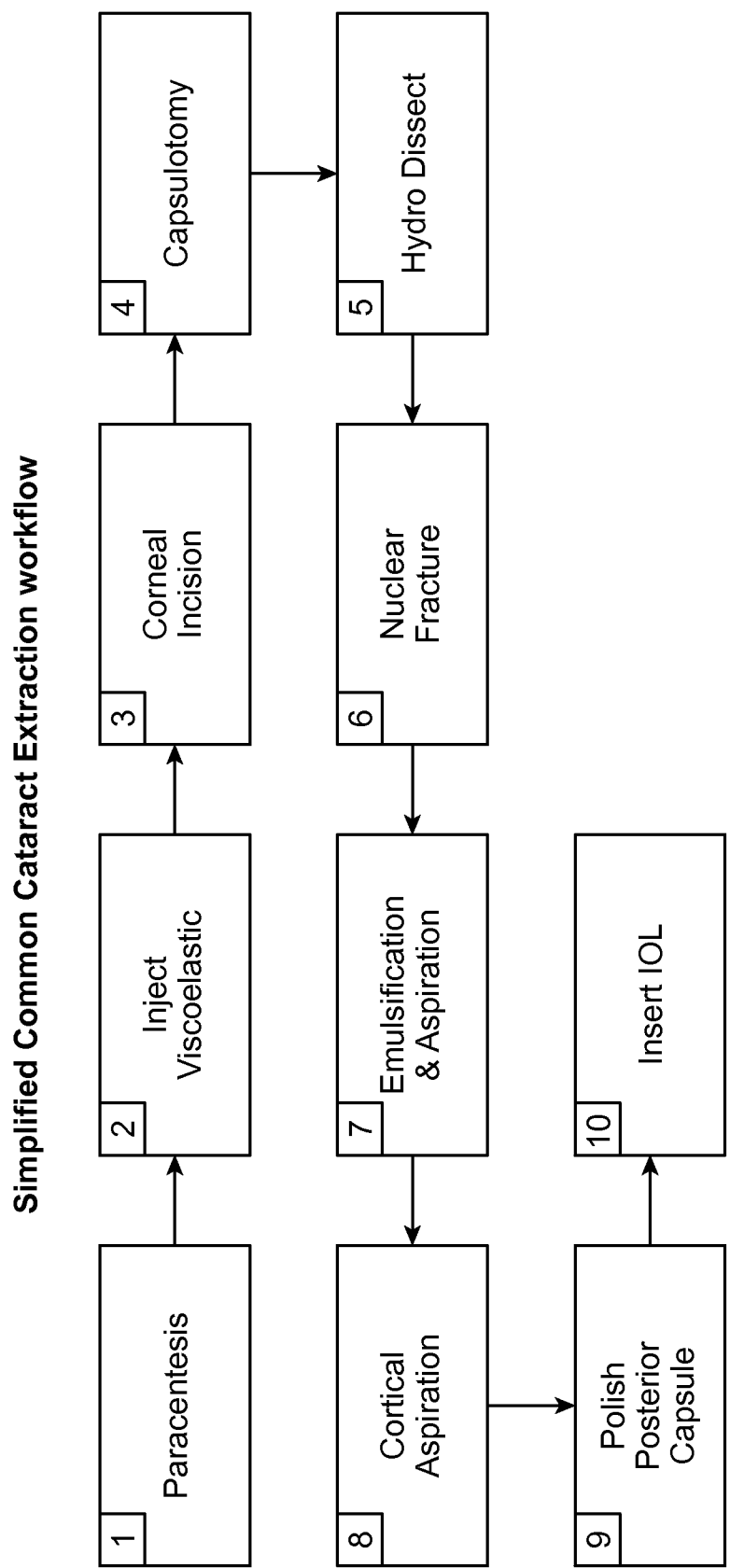
FIG. 8 is a common modern cataract extraction workflow.
Figure 10:
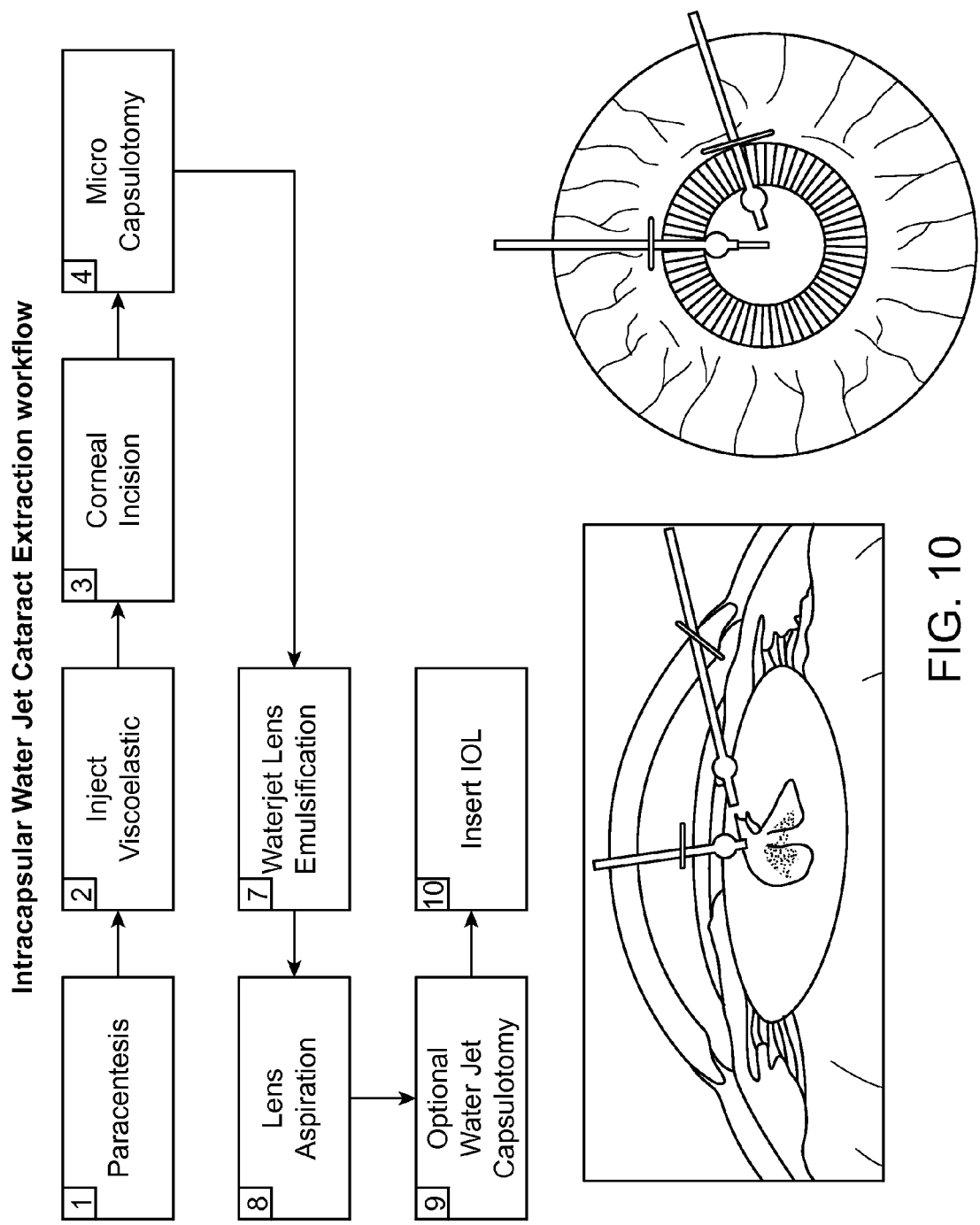
Figure 11:
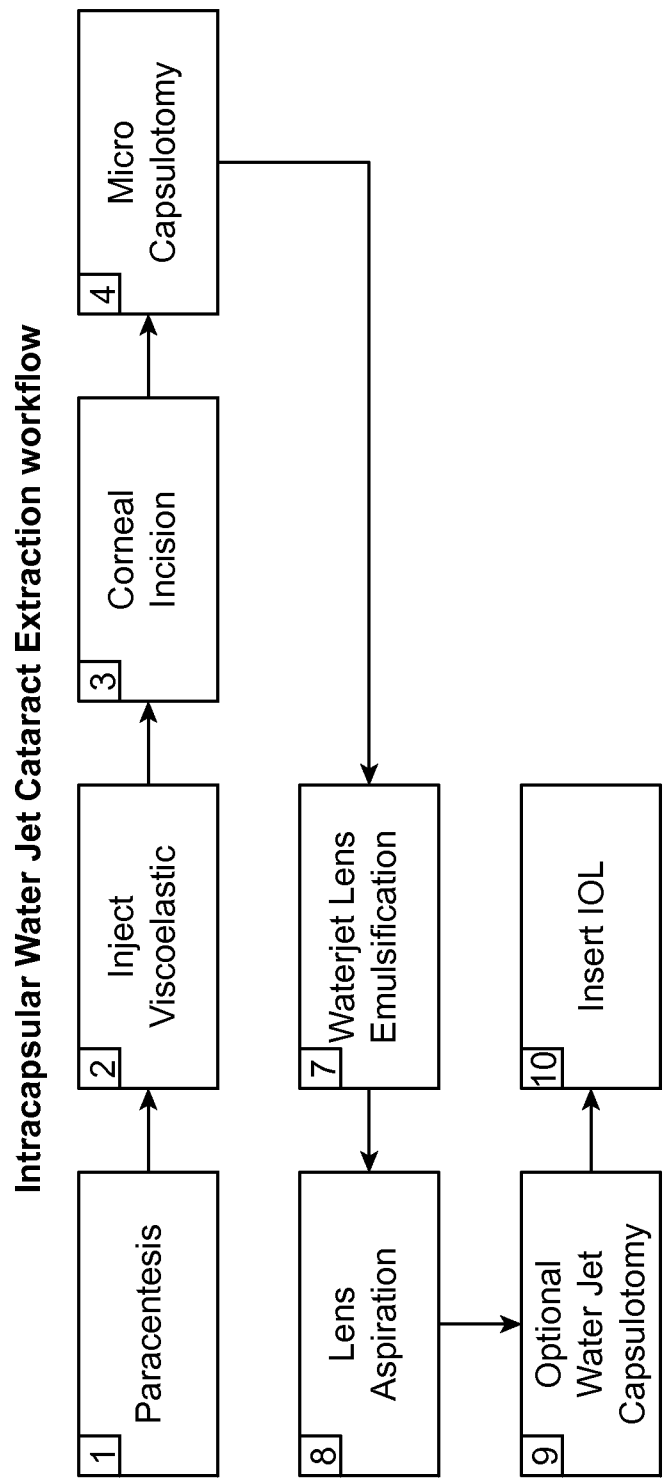

FIGS. 9-11 depict a method for a workflow based at least in part on utilizing the previous examples of a water jet apparatus or water jet system in manual or robotic system control, according to one embodiment of the present invention. The figures include descriptive text to facilitate understanding of the different workflow as compared to FIG. 8.

Figure 12:
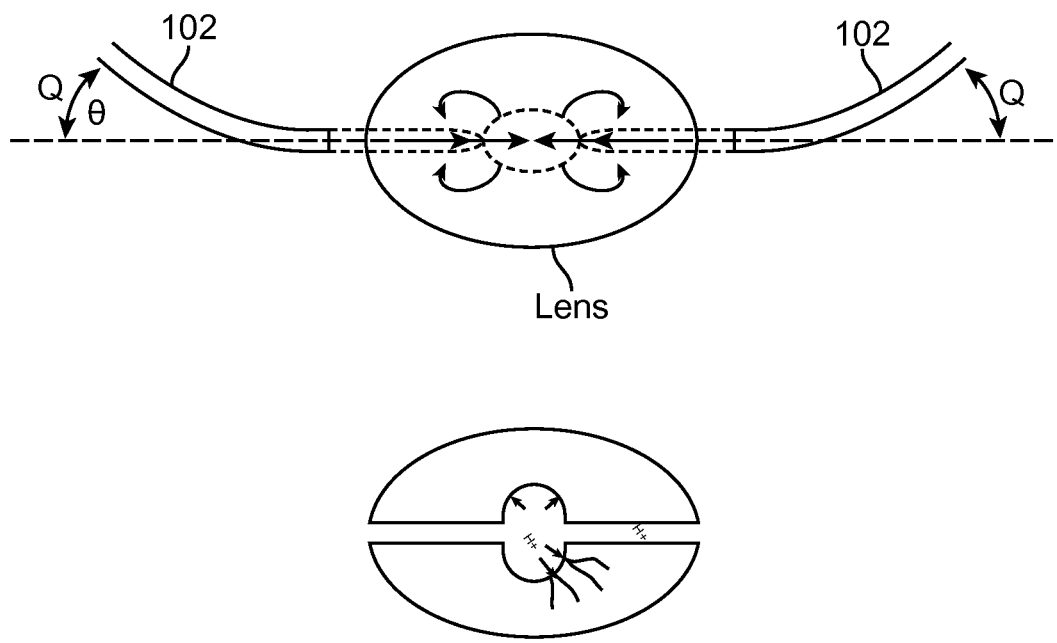
FIG. 12 depicts two water jet apparatus in a competing dual intersecting stream configuration, according to one embodiment of the present invention.

FIG. 12 depicts two water jet apparatus in a competing dual intersecting stream configuration, according to one embodiment of the present invention. In this configuration, a first and second water jet apparatus 102 are advancing toward the eye along an oblique intersecting angle, Q, into the anterior nuclear surface. For example, the water jet stream dissolves a channel as they progress. Consequently, this creates a turbulent core when they meet that starts disrupting from inside the lens outward due to the high pressure within the lens.

Figure 13:
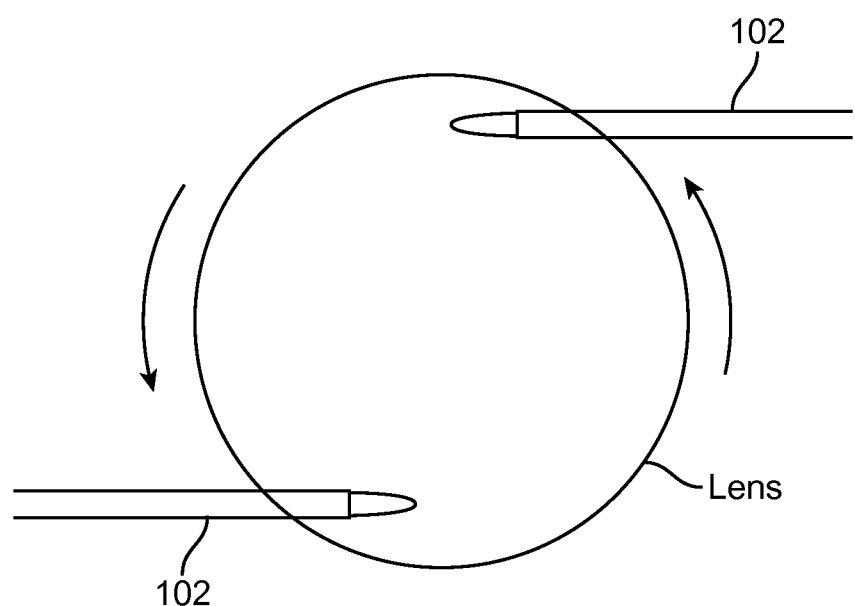
FIG. 13 depicts two water jet apparatus in an opposing and adjacent juxtaposed stream configuration.

FIG. 13 depicts two water jet apparatus in a opposing and adjacent juxtaposed stream configuration. In this embodiment, the configuration depicts two water jet apparatus 102 creating two opposing but adjacent juxtaposed streams to interact with tissue to remove the cataract buildup. In this representation, the waterjets cause a counterclockwise direction of the juxtaposed stream. However, the claimed subject matter is not limited to this direction and could be provided in an opposite direction as well.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A system to facilitate surgery, the system comprising:
a fluid jet instrument operatively coupled to an instrument drive mechanism via an instrument drive coupling mechanism comprising an instrument interface, the fluid jet instrument being configured to facilitate surgery and comprising a nozzle configured to generate a fluid jet that has a desired jet cutting area and a desired dispersive area; and
a flow rate control mechanism comprising a controller, a pump, a flow rate meter, and a throttle valve coupled together to form a feedback loop,
wherein the nozzle is configured to be controlled by the flow rate control mechanism to control a flow rate of the fluid jet and one or more of the desired jet cutting area or the desired dispersive area via the feedback loop, and
wherein the feedback loop comprises a feedback signal from the flow rate meter to the controller, a pump signal to the pump generated by the controller in response to the feedback signal, and a throttle valve signal to the throttle valve generated by the controller in response to the feedback signal, and
wherein the pump and the throttle valve combine to control the flow rate of the cutting fluid jet in response to the pump signal and the throttle valve signal, respectively.

2. The system of claim 1 wherein the fluid jet instrument is configured to aspirate fluid, and wherein the flow rate control mechanism further comprises an aspiration pump and aspiration flow rate meter operatively coupled to one another.

3. The system of claim 2, wherein the controller is configured to generate an aspiration control signal provided to the aspiration pump to control aspiration by the fluid jet instrument.

4. The system of claim 2, wherein the nozzle comprises an aspiration channel for the fluid instrument to aspirate fluid and a flush channel for the cutting fluid jet.

5. The system of claim 4, wherein the aspiration channel and the flush channel are coaxially disposed with respect to one another.

6. The system of claim 4, wherein the aspiration channel and the flush channel are adjacently disposed with respect to one another.

7. The system of claim 4, wherein the aspiration channel and the flush channel are separately disposed with respect to one another.

8. The system of claim 1, wherein the fluid jet instrument is configured to facilitate surgery in a fluid medium, and wherein one or more of the desired jet cutting area or the desired dispersive area are in the fluid medium.

9. The system of claim 8, wherein the fluid medium comprises saline.

10. The system of claim 1, wherein the fluid jet instrument is configured to facilitate surgery in an eye, and wherein one or more of the desired jet cutting area or the desired dispersive area are configured to be in a structure of the eye.

11. The system of claim 10, wherein the structure of the eye comprises a lens or lens capsule.

12. The system of claim 1, wherein one or more of the robotic arm or instrument drive mechanism is coupled to the flow rate control mechanism.

13. The system of claim 1, wherein the flow rate control mechanism further comprises at least one of a pressure vessel, a pressure gauge, or an aspiration pump coupled to the feedback loop.

14. The system of claim 1, further comprising a fluid flow path from the pump to the nozzle.

15. The system of claim 14, wherein the flow rate meter is downstream of the throttle valve in the fluid flow path.

16. The system of claim 14, wherein the flow rate meter and the throttle valve are downstream of the pump in the fluid flow path.

17. The system of claim 1, wherein one or more of the instrument drive mechanisms or a robotic arm coupled to the instrument drive mechanism is configured to be controlled based on localization techniques applying at least one of 3D imaging, MRI, CT, ultrasound, or intra-operative OCT.

18. The system of claim 1, wherein the fluid jet instrument is configured to facilitate surgery in an enclosed operative space within a bodily organ, and wherein one or more of the desired jet cutting area or the desired dispersive area are configured to be in a structure of the bodily organ.

19. The system of claim 18 wherein the fluid jet instrument is configured to aspirate one or more of fluid or particles from the enclosed operative space.

* * * * *